United States Patent
Collins

(10) Patent No.: US 7,537,917 B2
(45) Date of Patent: May 26, 2009

(54) MICROWAVE ASSISTED PCR AMPLIFICATION OF DNA

(76) Inventor: Michael J. Collins, 10225 Thomas Payne Rd., Charlotte, NC (US) 28277

(*) Notice: Subject to any disclaimer, the term of this patent is extended or adjusted under 35 U.S.C. 154(b) by 0 days.

(21) Appl. No.: 11/278,286

(22) Filed: Mar. 31, 2006

(65) Prior Publication Data

US 2007/0231798 A1 Oct. 4, 2007

(51) Int. Cl.
C12P 19/34 (2006.01)
C12Q 1/68 (2006.01)
(52) U.S. Cl. .......................... 435/91.2; 435/6
(58) Field of Classification Search .................. None
See application file for complete search history.

(56) References Cited

U.S. PATENT DOCUMENTS

| | | | |
|---|---|---|---|
| 4,683,195 A | | 7/1987 | Mullis et al. |
| 4,683,202 A | * | 7/1987 | Mullis .................. 435/91.2 |
| 4,889,818 A | * | 12/1989 | Gelfand et al. ............. 435/194 |
| 5,302,347 A | | 4/1994 | Van Den Berg et al. |
| 6,403,939 B1 | * | 6/2002 | Fagrell ..................... 219/709 |
| 6,744,024 B1 | | 6/2004 | Hayes et al. |
| 6,773,901 B2 | | 8/2004 | Uematsu et al. |
| 6,917,023 B2 | | 7/2005 | Hayes et al. |
| 2002/0117498 A1 | | 8/2002 | Jennings |
| 2003/0089706 A1 | | 5/2003 | Jennings |
| 2004/0101441 A1 | | 5/2004 | Jennings |
| 2004/0179977 A1 | | 9/2004 | Hargett, Jr. et al. |
| 2005/0045625 A1 | | 3/2005 | Collins, Jr. et al. |
| 2005/0045626 A1 | | 3/2005 | Collins, Jr. et al. |
| 2005/0121307 A1 | | 6/2005 | Hargett, Jr. et al. |

FOREIGN PATENT DOCUMENTS

| | | |
|---|---|---|
| JP | 2005021120 A | 1/2005 |
| WO | WO 9515671 A | 6/1995 |
| WO | WO 9515671 | 8/1995 |
| WO | WO 9806876 | 2/1998 |
| WO | WO 9849340 | 11/1998 |
| WO | WO 03093407 A | 11/2003 |
| WO | WO03093407 A1 * | 11/2003 |
| WO | WO 03093407 A1 * | 11/2003 |

OTHER PUBLICATIONS

Fermer et al. (Microwave-assisted high-speed PCR Eur J Pharm Sci. Feb. 2003;18(2):129-32).*
Orrling et al. ("An efficient method to perform milliliter-scale PCR utilizing highly controlled microwave thermocycling" Chem Commun (Camb). Apr. 7, 2004;(7):790-1).*
Fermer et al, "Microwave-assisted high-speed PCR," European Journal of Pharmaceutical Sciences, vol. 18, No. 2, Feb. 2003, pp. 129-132.
Orrling et al, "An efficient method to perform milliliter-scale PCR utilizing highly controlled microwave thermocycling," Chemical Communications (Cambridge, England), Apr. 7, 2004, No. 7, pp. 790-791.
European Search Report for Application No. EP 07104375; A. Werner, Authorized Officer, Date of Mailing: Jul. 4, 2007; 3 pgs.
Ohhara et al, "Direct PCR of Whole Blood and Hair Shafts by Microwave Treatment," BioTechniques, vol. 17, No. 4 (1994), pp. 726-728.
Roche Molecular Diagnostics, "PCR Explained" [Online], http://www.Roche-Diagnostics.com/ba_rmd/pcr_explained02.html, Feb. 22, 2006.

* cited by examiner

*Primary Examiner*—Kenneth R. Horlick
*Assistant Examiner*—Christopher M. Babic
(74) *Attorney, Agent, or Firm*—Summa, Additon & Ashe, P.A.

(57) ABSTRACT

A method of microwave assisted nucleic acid amplification by PCR is disclosed. The method includes denaturing, annealing, and extending a nucleic acid sample, with at least the denaturing and extension steps being carried out under the influence of microwave radiation, while preventing the temperature of the sample from varying more than 40° C. from start to finish, and while maintaining the temperature of the sample from start to finish at no more than 60° C.

16 Claims, No Drawings

MICROWAVE ASSISTED PCR AMPLIFICATION OF DNA

BACKGROUND

The present invention relates to the enzyme catalyzed replication of large biological molecules and in particular relates to microwave assisted PCR amplification of DNA.

As well understood by those of ordinary skill in this art, and indeed to some extent by the layperson, the DNA molecule carries the genetic code that determines the physical features and functions of biological organisms, including those of human beings. The DNA molecule can be described as a double helix in which phosphate groups and sugars form two respective chains ("backbones") while amino groups (typically referred to as "bases") attached to the chains form hydrogen bonds with one another that connect the two chains ("strands") together. Because the bases form hydrogen bonds with geometric specificity, the bases always connect to one another in specific pairs. As a result, when the strands separate (or are separated), each provides a pattern of successive bases that form a template for reconstructing the entire DNA molecule from either, or both, of the separated strands. This process is, of course, carried out naturally in living organisms and is referred to as "replication."

In many circumstances, DNA is available in extremely small quantities. When such quantities are too small for identification or analysis, the DNA can be amplified by a laboratory practice that is patterned after natural DNA replication and that is referred to as the "polymerase chain reaction" and typically abbreviated as "PCR." PCR is generally carried out in three steps with one set of such steps being referred to as a "cycle." For comparison purposes, PCR results are usually best understood in terms of the results that can be obtained after at least about 30 PCR cycles.

U.S. Pat. Nos. 4,683,202 and 4,683,195 are often referred to as seminal references in describing PCR technology. U.S. Pat. No. 4,683,202 has been cited in over 1400 later U.S. Patents and U.S. Pat. No. 4,683,195 has been cited in over 1300 later U.S. Patents. Accordingly, the basic, and to a great extent the sophisticated, aspects of PCR amplification are well understood in this art and will not be described in detail other than is necessary to describe the invention herein.

The capacity to amplify DNA creates the related capacity to evaluate DNA for a number of diagnostic purposes. PCR can produce DNA samples of sufficient size to detect the presence or absence of particular items, typically a virus, a bacterium, or even a particular sequence of genetic material. PCR technology thus provides the capacity to detect infectious diseases and genetic characteristics including genetic variations and mutations. PCR is accordingly the basis for a number of clinical diagnostic tests for infectious diseases. Because PCR is extremely sensitive, in some cases it can also quantify (in addition to identifying) the amount of a particular virus in a person's blood, thus providing the capacity to monitor either the progression of a disease or its response to treatment. For the same reasons, PCR is extremely valuable in blood screening (i.e., donated blood) to identify or preclude the presence of infectious agents. From a genetic testing standpoint, PCR can identify a genetic predisposition toward particular diseases or conditions and in some cases can, or is expected to, identify or predict how a particular person will respond to a specific pharmaceutical (or other medical) treatment. See, Roche Molecular Diagnostics, Applications of PCR [Online], www.Roche-Diagnostics.com/ba_rmd/pcr_applications.html, March 2006.

DNA amplification also provides a relatively straightforward method of purifying a particular DNA segment that is otherwise present in a bulk material. If the amplification is carried out to a sufficient extent, the desired DNA product becomes a proportionally overwhelming component of the mixture, thus effectively reducing other contaminants to trivial amounts. See, Cantor, *Genomics*, John Wiley and Sons, Inc., 1999, at page 98.

As yet another advantage, PCR amplification of DNA can be used to create libraries of DNA that in turn can be used in combinatorial chemistry techniques for a variety of analytical, diagnostic or synthesis purposes.

Each PCR cycle includes the steps of (i) denaturation, (ii) annealing, and (iii) extension. Prior to denaturation, the DNA which is to be amplified is mixed in combination with primer molecules and enzymes.

"Denature" refers to the step of separating the DNA double helix into two individual strands with a goal of at least 99 percent completion. In typical PCR techniques, the denaturation step is carried out by heating the DNA to a temperature of between about 90 and 105° C. for a period of between about one and ten minutes, at which temperature the double strand opens to form single stranded DNA. This temperature also tends to stop reactions from the previous cycle.

"Annealing" refers to the step of adding specific primers to the separated DNA strands. Primers are required because the DNA enzymes cannot start DNA chains from scratch. Instead, the primer is required to determine the location along a particular DNA template at which the synthesis of the complementary strand will begin. Thus, specific desired DNA regions can be selectively amplified by using appropriate primers. Primers are short, synthetic sequences of single-stranded DNA, typically consisting of 20-30 bases, with a labeled end structure to aid in identification. They are generally specific for the target region of the DNA of the organism. In most PCR amplifications, two primers are used, one for each of the complementary single DNA strands that was produced during denaturation. The art is replete with examples of specific primers that have been developed to amplify specific types or portions of DNA.

The annealing step is carried out by lowering the temperature to between about 50 and 60° C. at which point the primers attach themselves in an appropriate fashion and amount to the individual DNA strands that were previously separated.

Once the annealing step has been carried out to an extent that binds the primers to the DNA strands, the temperature is again raised, typically to greater than 70° C. and an enzyme is used to help replicate the DNA strands. The enzyme synthesizes new double-stranded DNA molecules by facilitating the joining of the complementary nucleotides (i.e., the sugar joined to a base and to a phosphate group) in solution.

As a result, at the end of the first PCR cycle, two new DNA strands are present, each of which is identical to the original target DNA strand that was denatured and primed.

As noted above, a typical DNA amplification requires about 30 PCR cycles. From a time standpoint, the denaturation step typically takes about two minutes, the cooling step that anneals the primers onto the separate strands likewise takes about two minutes, and the extension step again takes about two minutes. Thus each PCR cycle takes on the order of about six minutes. In turn, a 30 cycle amplification will take between about two and three hours of total time.

As in any other process of scientific or commercial importance, reducing the time required for any one or more of the steps will likewise reduced the time required to carry out one cycle and thus reduce the time required for the total amplification. Furthermore, because each step in the PCR cycle is a thermal step, the time required will typically increase based upon increased amounts of material.

Accordingly, the time required to carry out any one or more of the PCR steps can create a corresponding disadvantage in DNA amplification and replication.

As another factor, because the typical PCR cycle (e.g. using Taq polymerase; Cantor, supra) includes moving the temperature of the compositions upwardly (denaturation at 92-96° C. for 30-60 seconds) and then downwardly (annealing at 55-60° C. for about 30 seconds) and then upwardly again (extension at about 72° C. for about 60 seconds), fluctuations in the temperatures can cause undesired modifications that are rapidly magnified. As generally well understood in this art, a typical PCR instrument uses a plurality of tube holders or microtitre plate holders that are temperature controlled by heating elements and cooling baths, or by thermoelectric heating and cooling, or by forced convection heating and cooling, or by switching between and among water baths. See Cantor, supra at page 103.

In short, temperature swings during PCR amplification can create or increase undesired modifications.

As yet another factor, because the denaturing step requires the relatively higher temperature, the other compounds present in the PCR sample, and most typically the extension enzymes, must remain stable at these elevated denaturation temperatures. Accordingly, these temperature requirements effectively limit the selection of available enzymes for PCR.

In particular, the Taq polymerase is used because it can generally withstand the DNA denaturation temperatures. In conventional PCR, using an enzyme that cannot withstand the denaturation temperatures requires that fresh enzyme he added after every cycle, thus increasing the manipulative complexity of the process and the time required.

Although using high temperature enzymes such as Taq eliminates the need to add fresh enzyme after every cycle, such high temperature enzymes, including Taq, raise different problems. For example, the Taq enzyme lacks a 3' to 5' exonuclease activity. Such activity is informally referred to as a "proofreading" capability in which the enzyme is able to identify misplaced bases and replace them with correct bases in the desired positions (in a manner consistent with natural organisms). If the PCR cycle misidentifies or misplaces bases, it will, of course, replicate something other than the target sequence. Because of the nature of amplification, such errors will be significantly magnified over the course of many cycles.

As a second problem, standard PCR is typically limited to target sequences of between about 2000 and 3000 base pairs. Conducting PCR on larger targets (e.g., up to 50,000 base pairs) tends to require slower heating cycles and special enzymes that may not be amenable (or as amenable) to conventional PCR cycles.

Accordingly, a lack of fidelity and size limitations in the target sequences remain as disadvantages in conventional PCR.

SUMMARY

In one aspect the invention is a method of carrying out PCR amplification of DNA comprising maintaining a composition of DNA, primer (or primers), and replicating enzyme (or enzymes) at a temperature less than about 60° C., directing a first pulse of microwave radiation to the DNA sufficient to denature the DNA while maintaining the DNA at a temperature less than about 60° C., annealing the primer onto the separate DNA strands while maintaining the DNA at a temperature less than about 60° C., and directing a second pulse of microwave radiation to the annealed DNA strands sufficient to replicate and extend the primary sequence while maintaining the DNA at a temperature less than about 60° C.

In another aspect, the invention is a method of microwave assisted nucleic acid amplification by PCR comprising denaturing, annealing, and extending a nucleic acid sample, with at least the denaturing and extension steps being carried out under the influence of microwave radiation, while preventing the temperature of the sample from varying more than 40° C. from start to finish, and while maintaining the temperature of the sample from start to finish at no more than 60° C.

In another aspect, the invention is a method of carrying out PCR DNA amplification cycles comprising directing a first pulse of microwave radiation to a composition of DNA and primer and replicating enzyme that is sufficient to denature the DNA in the presence of a replicating enzyme that denatures at temperatures above about 60° C., annealing the primer onto the separate DNA strands, directing a second pulse of microwave radiation to the annealed DNA strands sufficient to replicate and extend the primary sequence, and repeating the denaturing, annealing and extension cycle at least twice without refreshing the replicating enzyme.

The foregoing and other objects and advantages of the invention and the manner in which the same are accomplished will become clearer based on the followed detailed description.

DETAILED DESCRIPTION

The present invention is a method of carrying out PCR amplification of DNA. As well understood in the art, PCR amplification can be carried out on specific nucleic acid sequences and on DNA or RNA. In its broadest sense, the invention can amplify any one or more desired specific nucleic acid sequences found in a nucleic acid, and in particular in DNA. Accordingly, the invention will be understood in this relatively broad sense.

As will become clear from the description herein, the invention provides the capability to use combinations of enzymes (thus more closely following natural organisms), and can prevent the problems raised when the enzymes degrade, either over time or because of temperature or both, and provides the opportunity to do low or moderate temperature PCR at cycle times faster than conventional high temperature PCR.

The nature and preparation of DNA samples intended for PCR application are generally well understood in the art. The DNA to be reproduced (typically referred to as the "target") is selected along with the desired primers and enzymes. Following PCR amplification, the DNA is sampled in conventional fashion (e.g., gel electrophoresis, stained, and under ultraviolet light) to evaluate the results.

The method comprises the steps of maintaining a composition of DNA and primer(s) and replicating enzyme(s) at a temperature less than about 60° C. A first pulse of microwave radiation is directed to the DNA sufficient to denature the DNA while continuing to maintain the DNA at a temperature of less than about 60° C. The method next comprises the steps of annealing the primer onto the separate DNA strands while maintaining the DNA at a temperature less than about 60° C., and directing a second pulse of microwave radiation to the annealed DNA strands sufficient to replicate and extend the primary sequence while maintaining the DNA at a temperature less than about 60° C.

In particular embodiments, the method comprises amplifying the DNA with a replicating enzyme that denatures at temperatures above about 60° C. Stated differently, the method permits the use of enzymes that can be selected for purposes other than their capability of avoiding denaturing at the usual high temperatures (e.g., above 90° C.) used for denaturing DNA. In some embodiments, a replicating enzyme can be included that denatures at temperatures above about 45° C. In such cases, the method comprises maintaining the composition at a temperature below about 45° C. during the denaturing, annealing, and extension steps.

It will be understood that the temperatures referred to herein are those of the entire or "bulk" sample. The use of microwaves is understood to create small portions of the sample that may temporarily experience much higher temperatures. To date, however, any practical means for identifying such small portions, or the specific temperatures they reach, remains unavailable. Thus, as used herein, when a sample is maintained at a particular temperature, this represents the bulk temperature, and the presence of small portions that may occasionally exceed a recited temperature in a manner that cannot be observed, does not remove the sample from the overall description or from the scope of the claims.

Stated differently, bulk samples that remain within the indicated temperatures and temperature ranges herein fall within the invention and the claims even if small portions (which cannot be measured) theoretically or practically reach higher temperatures for temporary periods.

As will be further understood with respect to temperatures, every PCR amplification will typically begin with the starting materials at ambient (usually room) temperature. It will thus be understood that when the specification and claims refer to maintaining items at particular temperatures or within certain temperature ranges, this does not necessarily include the step of raising the temperature from ambient to the desired recited temperature. Stated differently, starting at room temperature and increasing the temperature of the sample to the temperatures described herein during the process as described herein falls within the scope of the invention and the claims.

In some embodiments, the method comprises carrying out the denaturing, annealing and extension steps concurrently on a plurality of compositions of DNA and primer(s) and replicating enzyme(s). The method can be carried out on a plurality of identical samples, or on at least two different samples, or on a larger plurality of different samples; e.g., the 96 samples typically used on a microtitre plate.

The method can comprise the step of annealing the primer at a temperature lower than the temperature of the denaturing step, or annealing the primer at a temperature lower than the temperature of the extension step, or both. Primers are generally well understood in the art and can be selected by persons of skill in the art without undue experimentation. It is generally well understood that the primers will be selected based upon their composition and length—i.e., factors particular to the desired amplification—and thus particular primers will not be described in detail herein.

The sources and availability of DNA, primers, and enzymes are likewise well understood in the art and can be obtained by those of skill in this art without undue experimentation, and indeed in some cases from conventional commercial vendors; e.g., the custom primer pairs and AMILTAQ GOLD® enzymes from Applied Biosystems, Foster City, Calif., USA.

Primers are also categorized in terms of their "melting" temperatures. In the primer context, "melting" is typically defined as the temperature at which half of the primer binding sites are occupied. Longer primers have higher melting temperatures. Shorter than desired primers tend to anneal at several positions on the relatively longer DNA template and thus tend to create non-specific copies. Alternatively, the higher melting primers require higher annealing temperatures which in turn can reduce the effectiveness of the enzyme. Accordingly, PCR primers typically include between about 15 and 40 nucleotides and have typical melting temperatures between about 55 and 65° C. Thus, the annealing step is typically carried out near, but not at the melting temperature; i.e. between about 50 and 60° C.

The cooling capability of the methods and instruments referred to herein provide the opportunity to energize the primers sufficiently to anneal in the desired amounts and positions at temperatures lower than conventional PCR. Stated differently, conventional PCR raises the temperature above 90° C. in order to denature the DNA and then specifically lowers the temperature to between about 50 and 60° C. to anneal the primers. The invention provides the capability to denature the DNA at much lower temperatures and to anneal the primers at lower temperatures with or without the application of the pulse of microwave energy during the annealing step.

In particular embodiments, the method comprises proactively cooling the composition of DNA and primer and replicating enzyme to maintain the desired temperatures during the denaturation, annealing and extension steps.

The proactive cooling step is typically carried out by cooling the sample (and most commonly the sample vessel to in turn cool the sample) with an inert gas or with a liquid.

An appropriate description of an apparatus and technique for proactively cooling chemical reactions while applying microwave radiation is set forth in commonly assigned U.S. Pat. Nos. 6,744,024 and 6,917,023 the contents of each of which are incorporated entirely herein by reference. A commercial instrument for carrying out microwave assisted chemical reactions while proactively cooling the reagents is available under the DISCOVER® COOLMATE™ trademark from the assignee herein, CEM Corporation, Matthews, North Carolina, USA.

As set forth in the above-incorporated patents, a single mode microwave cavity (i.e., a cavity that supports a single mode at the wavelength generated by the microwave source) offers the favorable capacity to accurately apply microwave energy to small samples such as those used in most PCR reactions (e.g. 0.1-1.0 ml). The use of single mode cavities has also been demonstrated for PCR amplification (e.g., Fermér, *Microwave-Assisted High-Speed PCR*, European Journal of Pharmaceutical Sciences, 18 (2003), pages 129-132).

The step of pulsing the microwave radiation is generally well understood in the art and refers to the use of a defined application of power for a defined non-continuous period of time. It also is intended to differentiate from the usual cycling of the application of microwave power that follows the normal 60 cycle frequency of alternating electric current in the United States (or other frequencies in other countries). Thus, in typical embodiments the step of pulsing the application of microwave radiation comprises applying a non-continuous pulse of between about 50 and 250 watts for no more than one second. The reaction is mass-transfer controlled, thus the time and power of the pulse depends upon the amount of material being amplified. Thus, those of skill in the art can select the relevant pulses without undue experimentation.

In another aspect, the invention is a method of microwave assisted nucleic acid amplification by PCR comprising the steps of denaturing, annealing, and extending a nucleating acid sample, with at least the denaturing and extension steps being carried out under the influence of microwave radiation, while preventing the temperature of the sample from varying more than 40° C. from start to finish and while maintaining the temperature of the sample from start to finish at no more than 60° C.

In some embodiments, the method comprises preventing the bulk temperature of the sample from varying no more than 20° C. from start to finish, and in some embodiments no more than 10° C. from start to finish.

In some embodiments the method comprises maintaining the temperature of the sample from start to finish at no more than 50° C., and in some embodiments no more than 45° C.

In this aspect, the method can comprise at least two cycles of denaturing annealing and extending, and more typically at least 30 cycles of denaturing, annealing and extending.

In the most common embodiments the amplification is carried out on a DNA sample, and including either single samples or (concurrent) multiple samples. In the case of multiple samples, the method can comprise concurrently extending identical samples of DNA or concurrently extending different samples of DNA. In some embodiments, the method can comprise extending at least 96 DNA samples as in the case of the use of a microtitre plate.

As in the previous aspect, the step of carrying out the cycle under the influence of microwave radiation comprises applying pulse radiation to the DNA sample, and most typically pulses of between about 50 and 250 watts for no more than one (1) second. Most typically, the method comprises applying a first pulse of microwave radiation for the denaturing step and applying a second pulse of microwave radiation for the extension step.

Because of the speed of microwave application, the method can includes carrying out at least 20 PCR cycles in less than one hour, and in some cases less than 30 minutes. Indeed, as a predictive example, when microwave pulses are used for the denaturing and extension steps (thus eliminating the time required to cool the sample for the annealing step), the entire cycle can be carried out in 5-10 seconds (or perhaps even less) which in turn translates to a 30 cycle amplification taking place in as little as 2-5 minutes.

The invention can be carried out in stepwise fashion by adding new reagents after each step, or simultaneously with all materials added at the initial step, or partially stepwise and partially simultaneously with compositions being added after a given number of steps.

The PCR reaction is typically carried out in the presence of a buffer that maintains an appropriate pH. For example, appropriate mixtures of potassium phosphate, magnesium chloride, and sodium chloride can be used to maintain a pH of about 7.5. A basic pH is not always desired, however, and in other techniques the pH can be maintained on the acid side; i.e. below 7.0.

In accordance with the results expected for conventional PCR, the invention is expected to produce amplification inefficiencies in the range of between about 0.6 and 0.9. As used herein, the efficiency E is as defined by Cantor, supra; i.e., $$P/S = (1+E)n,$$

where S is the amount of starting material, P is the amount of product and n is the number of cycles.

In the specification there has been set forth a preferred embodiment of the invention, and although specific terms have been employed, they are used in a generic and descriptive sense only and not for purposes of limitation, the scope of the invention being defined in the claims.

The invention claimed is:

1. A method of microwave assisted DNA amplification by PCR comprising:
   carrying out at least 20 PCR cycles, with each PCR cycle including the steps of,
   denaturing, annealing, and extending a DNA sample, including applying a first pulse of microwave irradiation of no more than one second to the denaturing step of the cycle and a second pulse of microwave irradiation of no more than one second to the extension step of the cycle;
   while preventing the temperature of the sample from varying more than 20° C. from start to finish during each PCR cycle; and
   while maintaining the temperature of the sample from start to finish at no more than 50° C. during each PCR cycle and between all of the at least 20 PCR cycles.

2. A method according to claim 1 comprising carrying out the 20 cycles in less than one hour.

3. A method according to claim 1 comprising carrying out the 20 cycles in less than 30 minutes.

4. A method according to claim 1 comprising an efficiency of 0.6 to 0.9.

5. A method according to claim 1 comprising amplifying the DNA with a replicating enzyme that denatures at temperatures above 60° C.

6. A method according to claim 1 comprising amplifying the DNA with a replicating enzyme that denatures at temperatures above about 45° C.

7. A method according to claim 1 comprising maintaining the DNA sample at a temperature below 45° C. during the denaturing, annealing and extension steps.

8. A method according to claim 1 comprising carrying out the denaturing, annealing and extension steps concurrently on a plurality of identical samples.

9. A method according to claim 1 comprising carrying out the denaturing, annealing and extension steps concurrently on at least two different samples.

10. A method according to claim 1 comprising annealing the primer at a temperature lower than the temperature of the denaturing step.

11. A method according to claim 1 comprising annealing the primer at a temperature lower than the temperature of the extension step.

12. A method according to claim 1 comprising proactively cooling the DNA sample to maintain the desired temperatures during the denaturation, annealing and extension steps.

13. A method according to claim 1 wherein the step of directing the first pulse or the second pulse comprises applying a pulse of between about 50 and 250 watts.

14. A method according to claim 1 comprising maintaining the desired temperature by proactively cooling the sample with an inert gas.

15. A method according to claim 1 comprising maintaining the desired temperature by proactively cooling the sample with a liquid.

16. A method according to claim 1 wherein the DNA sample includes a replicating enzyme, and further comprising carrying out the 20 PCR cycles without refreshing the replicating enzyme.

* * * * *

UNITED STATES PATENT AND TRADEMARK OFFICE
CERTIFICATE OF CORRECTION

PATENT NO. : 7,537,917 B2 Page 1 of 1
APPLICATION NO. : 11/278286
DATED : May 26, 2009
INVENTOR(S) : Michael J. Collins It is certified that error appears in the above-identified patent and that said Letters Patent is hereby corrected as shown below:

In the CLAIMS:

Column 8, lines 27-29 read:

6. A method according to claim 1 comprising amplifying the DNA with a replicating enzyme that denatures at temperatures above ~~about~~ 45° C.

Column 8, lines 27-29 should read:

6. A method according to claim 1 comprising amplifying the DNA with a replicating enzyme that denatures at temperatures above 45° C.

Signed and Sealed this

Fourteenth Day of July, 2009

JOHN DOLL
*Acting Director of the United States Patent and Trademark Office*